United States Patent [19]

Mills et al.

[11] Patent Number: 5,700,147

[45] Date of Patent: Dec. 23, 1997

[54] AIR CONTROLLED STERILE IRRIGATION SYSTEM (ACSIS)

[75] Inventors: Shannon E. Mills; Randy Shaffer; Michael T. Freeman; Thomas J. Plamondon; Barry L. Oakes, Jr., all of San Antonio, Tex.

[73] Assignee: The United States of America as represented by the Secretary of the Air Force, Washington, D.C.

[21] Appl. No.: 498,831

[22] Filed: Jul. 6, 1995

[51] Int. Cl.⁶ .................................................. A61C 1/02
[52] U.S. Cl. .............................. 433/98; 433/85; 433/101
[58] Field of Search ............................ 433/88, 99, 100, 433/101, 82, 84, 85, 87

[56] References Cited

U.S. PATENT DOCUMENTS

| | | | |
|---|---|---|---|
| 2,420,338 | 5/1947 | Page | 433/84 |
| 3,250,005 | 5/1966 | White | 433/85 |
| 3,842,504 | 10/1974 | Ricks | 433/84 X |
| 3,949,753 | 4/1976 | Dockhorn | 433/84 X |
| 4,276,023 | 6/1981 | Phillips et al. | 433/85 |
| 4,359,317 | 11/1982 | Strohmaier et al. | 433/82 |
| 5,261,816 | 11/1993 | Vames | 433/98 X |
| 5,338,194 | 8/1994 | Strohmaier | 433/84 X |

*Primary Examiner*—Nicholas D. Lucchesi
*Attorney, Agent, or Firm*—Fredric L. Sinder; Thomas L. Kundert

[57] ABSTRACT

A new apparatus and method for delivering sterile irrigating solution to dental sites during restorative and surgical procedures is disclosed. A new sterilizable handpiece line adapter is connected between prior art dental handpieces and dental unit air-water hoses. The handpiece line adapter includes an input port for sterile irrigating solution and an outlet port for the sterile irrigating solution replacing a prior art outlet port for tap water. A standard IV bag containing sterile irrigating solution is pressurized with a standard infuser bag. Standard IV tubing connects the IV bag to the input port of the line adapter. An air-controlled, normally-closed pinch valve girdles part of the IV tubing. The pinch valve is connected to a spare outlet of a standard foot pedal controlled dental unit so that, when the foot pedal is depressed to operate the dental handpiece, the pinch valve automatically opens to allow delivery of sterile irrigating solution from the IV bag.

9 Claims, 2 Drawing Sheets

AIR CONTROLLED STERILE IRRIGATION SYSTEM (ACSIS)

RIGHTS OF THE GOVERNMENT

The invention described herein may be manufactured and used by or for the Government of the United States for all governmental purposes without the payment of any royalty.

BACKGROUND OF THE INVENTION

The present invention relates generally to air driven high speed dental handpieces and sonic scalers, and more specifically to a air controlled sterile irrigation system for providing sterile irrigating solution to such handpieces and the like for restorative and surgical procedures.

For reasons of effectiveness and convenience, high speed rotor handpieces as well as sonic and ultrasonic scalers are widely used by periodonists and general dentists for surgical procedures. All of these devices require a water source for cooling and irrigation of dental operative sites. The source of this water is almost invariably municipal tap water delivered through small bore plastic water lines inside dental units. These dental unit water lines are conducive to the formation of bacterial biofilms and have been shown to harbor high levels of potentially pathogenic microorganisms. Current methods for controlling this intrinsic contamination are technique sensitive and can, at best, provide only potable water. Although this water may be suitable for most non-surgical procedures, it does not meet current standards of care for surgical procedures, procedures during which an opening in tissue is usually made, and for which only sterile irrigating solutions are recommended. Delivery of sterile solutions requires a sterile pathway from the source to the handpiece. Since dental unit water lines cannot be sterilized, an independent sterile delivery system is needed.

Current methods for surgical irrigation in dental procedures include manual bulb or syringe irrigation or the use of high cost surgical handpiece systems. Although manual irrigation offers a low technology alternative, it is time and labor insensitive and its effectiveness is highly dependent on the skill of ancillary personnel. Dedicated oral surgery and implant handpieces are either electrically powered or use high pressure compressed air or nitrogen separate from the dental unit delivery system. Many of these devices incorporate some method for sterile irrigation of surgical sites. Most use a peristaltic infusion pump and disposable or autoclavable tubing. At least one system uses an electrically operated pinch valve. Electronic foot or hand operated controls regulate the operation of the pump mechanism. Prepackaged IV fluids are most often used to supply irrigating solutions. Those costly, specialized systems are intended for surgical use only and for that reason are rarely used in general practice settings.

There is only one commercial system currently available that is compatible with air driven high speed handpieces or sonic scalers. The STERIWATER. system, available from Palisades Dental, Tenafly, N.J., replaces a conventional dental unit with a relatively large, complicated and expensive autoclavable control mechanism. The entire assembly, including water reservoirs and all tubing, must be autoclaved between procedures. A true sterile pathway is not assured since non-sterile filtered air is used to force solutions from the autoclavable reservoir.

Although it is relatively simple to adapt a dental handpiece to accept sterile irrigation lines, a major limitation to effectiveness is the lack of a method for automatically controlling the flow of irrigating solutions. The result is an awkward and often messy procedure.

Thus it is seen that there is a need for a relatively simple, low cost, automatically controlled sterile irrigation system that can be added to standard dental handpieces for providing sterile irrigating solution to dental treatment sites during oral surgery and restorative procedures.

It is, therefore, a principal object of the present invention to provide an apparatus for delivering sterile irrigating solution through a standard dental handpiece and for automatically controlling the flow of sterile irrigating solution to the dental handpiece.

It is another object of the present invention to provide an apparatus for delivering sterile irrigating solution that is easily sterilizable, such as by autoclaving.

It is a feature of the present invention that it controls the flow of sterile irrigating solution with the same foot control as is used to control the dental handpiece, thus not only making the flow of sterile irrigating solution automatic with the use of a dental handpiece, but also hands-free.

It is another feature of the present invention that it helps eliminate the potential for contamination of dental treatment sites with the high levels of bacteria known to accumulate in dental unit water lines.

It is another feature of the present invention that it can administer any sterile solution that can be contained in a standard plastic IV bag or bottle.

It is an advantage of the present invention that its control mechanism does not require sterilization, making it more readily available for use and reducing the likelihood of sterilization related failure.

It is another advantage of the present invention that it uses readily-available, off-the-shelf supplies.

It is a further advantage of the present invention that it is compact, portable and can be installed on virtually any modern dental unit in moments.

These and other objects, features and advantages of the present invention will become apparent as the description of certain representative embodiments proceeds.

SUMMARY OF THE INVENTION

The present invention provides a new apparatus and method for providing sterile irrigating solution to dental handpieces and the like for restorative and surgical procedures. The breakthrough discovery of the present invention is that present-day dental handpieces can be easily enhanced by installing between a standard dental handpiece and a handpiece hose a sterilizable in-line adapter incorporating an input port for sterile irrigating solution, adding a pinch valve for a sterile hose between a source of sterile irrigating solution and the sterilizable in-line adapter input port, and, controlling the pinch valve with the same air that drives the dental handpiece.

Accordingly, the present invention is directed to an air controlled sterile irrigation system for providing sterile irrigating solution for dental procedures, comprising a sterilizable line adapter for connecting between a dental handpiece and a dental handpiece hose, the line adapter including an inlet port for receiving sterile irrigating solution and an outlet port for delivering sterile irrigating solution to the dental handpiece, and an air operated pinch valve for controlling the flow of sterile irrigating solution through an irrigating solution hose connected between a source of sterile irrigating solution and the inlet port for the sterilizable line adapter. The system may include a dental unit for supplying pressurized air to the dental handpiece, wherein the dental unit supplies pressurized air to the pinch valve at the same time it supplies pressurized air to the dental handpiece. The sterilizable line adapter may be adapted for connecting to a 4-hole ISO (International Standards Organization) dental unit air-water hose and may block the flow of water and chip air from the air-water hose through the line adapter. The air operated pinch valve may comprise a resiliently biased pincher for pinching closed the irrigating solution hose, an inlet for receiving pressurized air from a standard dental unit, and an air-controlled actuator connected to the pincher such that, when pressurized air is delivered through the inlet to the actuator, the actuator pushes the pincher against its resilient bias to incrementally open the irrigating solution hose. The system may also include a foot pedal control for connecting to a standard dental unit for controlling the delivery of pressurized air to the actuator.

The present invention is also directed to a sterile irrigation system for providing sterile irrigating solution for dental procedures, comprising a sterilizable line adapter for connecting between a dental handpiece and a dental handpiece hose, the line adapter including an inlet port for receiving sterile irrigating solution and an outlet port for delivering sterile irrigating solution to the dental handpiece, and a pinch valve for controlling the flow of sterile irrigating solution through an irrigating solution hose connected between a source of sterile irrigating solution and the inlet port for the sterilizable line adapter. The system may include a dental unit for supplying power to the dental handpiece, wherein the dental unit supplies power to the pinch valve at the same time it supplies power to the dental handpiece.

The present invention is further directed to a method for providing sterile irrigating solution to a dental site for surgical and restorative procedures, comprising the steps of providing a sterilizable line adapter connected between a dental handpiece and a dental handpiece hose, the line adapter including an inlet port for receiving sterile irrigating solution and an outlet port for delivering sterile irrigating solution to the dental handpiece, providing an air operated normally-closed pinch valve girdling an irrigating solution hose connected between a source of sterile irrigating solution and the inlet port for the sterilizable line adapter, wherein the pinch valve is connected through an air hose to a dental unit and wherein the dental unit is controlled by a controller for controlling the supply of pressurized air to the dental handpiece, and activating the controller to deliver pressurized air to the dental handpiece and simultaneously deliver pressurized air to the pinch valve to release the pinch valve and permit the flow of sterile irrigating solution through the irrigating solution hose into the inlet port for the line adapter and out the outlet port into the dental handpiece. A foot control may be used as the dental unit controller.

BRIEF DESCRIPTION OF THE DRAWINGS

The present invention will be more clearly understood from a reading of the following detailed description in conjunction with the accompanying drawings wherein.

DETAILED DESCRIPTION

Figure 1:
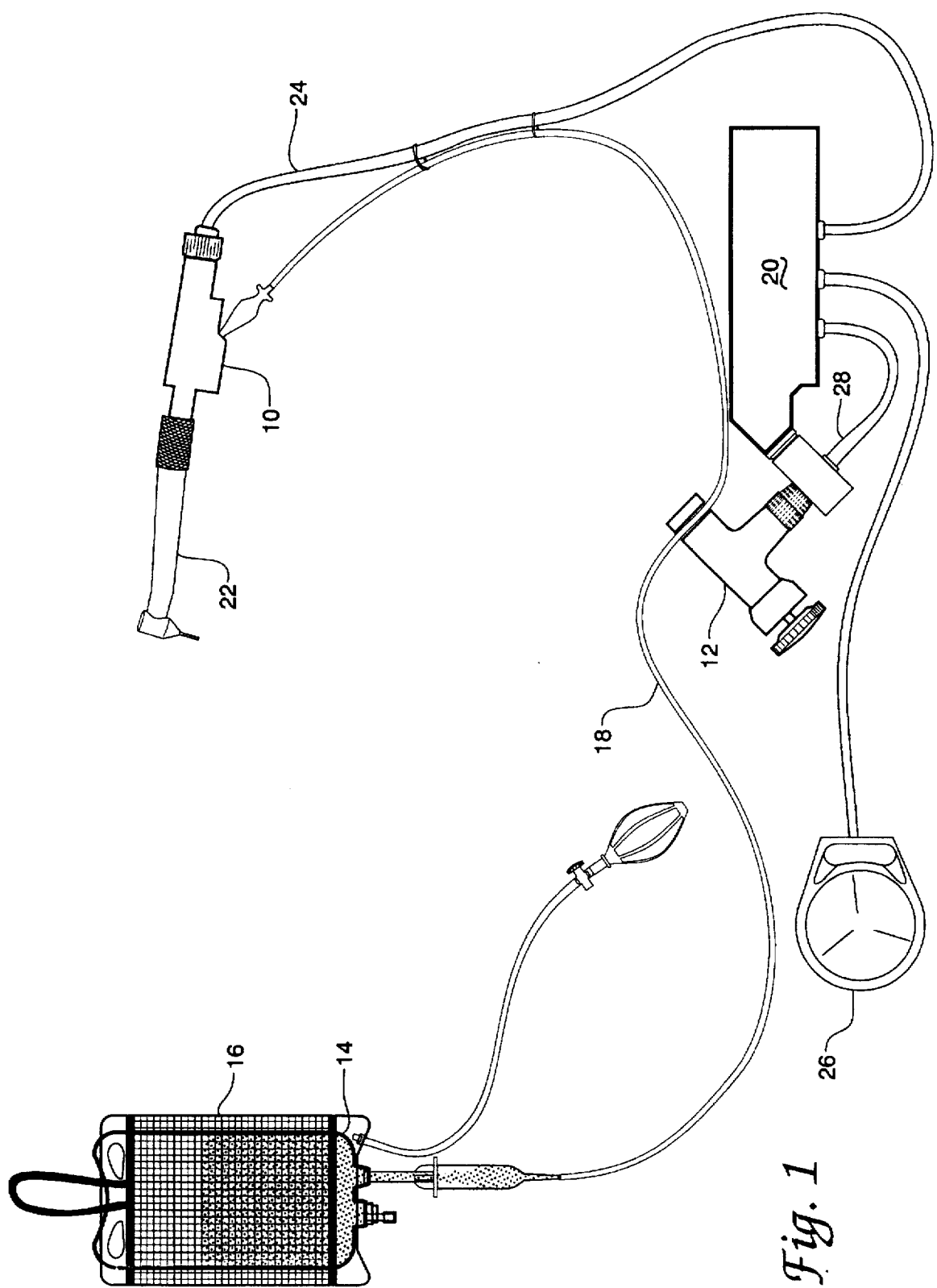
FIG. 1 is a diagrammatic view of an air controlled sterile irrigation system made according to the teachings of the present invention.

Referring now to FIG. 1 of the drawings, there is shown a diagrammatic view of an air controlled sterile irrigation system made according to the teachings of the present invention. The primary components of the sterile irrigation system are a handpiece line adapter 10, a pinch valve 12, an IV bag 14 containing sterile irrigating solution, a pressure infuser bag 16, and IV tubing 18 connecting IV bag 14 to handpiece adapter 10. The irrigation system attaches to standard dental unit components comprising a dental unit 20 (drawn smaller than scale in this figure), a high speed dental handpiece 22, a dental unit air-water hose 24 and a dental unit foot control 26. A spare dental unit air hose 28 is connected from dental unit 20 to pinch valve 12. Dental units, such as dental unit 20, generally have at least three outlets, of which normally only two are used.

Figures 2, 3, 4:
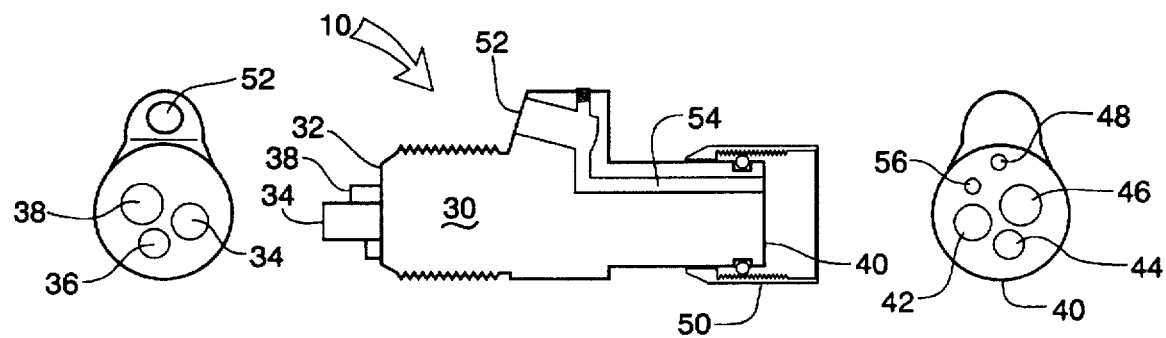
FIG. 2 is a partially sectional view of a sterilizable handpiece line adapter made according to the teachings of the present invention.
FIG. 3 is an end view of the handpiece hose-connecting end of the sterilizable handpiece line adapter of FIG. 2.
FIG. 4 is an end view of the handpiece-connecting end of the sterilizable handpiece line adapter of FIG. 2; and, FIG. 5 is a sectional view of an air operated pinch valve assembly made according to the teachings of the present invention.

FIG. 2 is a partially sectional view of sterilizable handpiece line adapter 10. Line adapter 10 includes a body 30, a hose end 32 having male ports 34, 36 and 38, a handpiece end 40 having female ports 42, 44, 46 and 48, a standard dental handpiece threaded coupler 50, an IV connector port 52 and a sterile water line 54.

Hose end 32 of line adapter 10 connects to dental unit air-water hose 24. Dental unit air-water hose 24 is a standard 4-hole ISO (International Standards Organization) dental unit air-water hose. The four holes, or channels, of a standard 4-hole dental unit air-water hose are for incoming drive air, exhaust drive air, tap water and chip air. Chip air is often mixed with tap water to make an aerosol mist. Chip air is useful for routine dental procedures and is safe when so used because there are no tissue openings into the body during those routine dental procedures. During surgical procedures, however, in addition to the risk of contamination, the presence of chip air can lead to an embolism. A standard 4-hole air-water hose generally will also include a fifth channel for a fiber optic cable. Hose end 32 of line adapter 10, as shown in FIG. 3, includes port 34 for incoming drive air, port 38 for exhaust drive air and port 36 for a fiber optic line. Hose end 32 does not include openings or ports for tap water and chip air which are blocked at the interface between hose end 32 and air-water hose 24. A neoprene gasket, not shown, prevents leaking. Also, when in use, standard dental units can and should be set to not send tap water or chip air.

Handpiece end 40 of line adapter 10 connects to dental handpiece 22. Dental handpiece 22 is a standard 4-hole ISO air driven handpiece or scaler. Handpiece end 40, as shown in FIG. 4, includes port 42 for incoming drive air, port 46 for exhaust drive air, port 44 for a fiber optic line, a port 56 for chip air and port 48 for sterile water. Port 48, which normally supplies tap water to a dental handpiece, now connects to IV connector port 52. Female port 56 for chip air is not needed for chip air, but needs to be present to make the connection with the male ports of handpiece 22.

Figure 5:
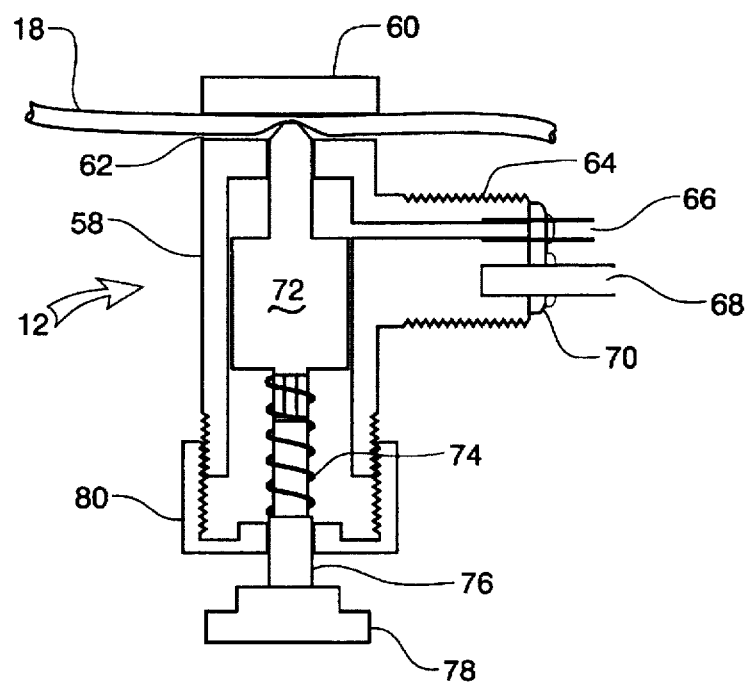

FIG. 5 is a sectional view of a preferred embodiment for an air operated pinch valve 12. Pinch valve 12 includes a pinch valve body 58, a cover plate 60, a tubing channel 62, an air hose attachment fitting 64, a pressurized air inlet 66, a pressurized air exhaust tube 68, a fitting gasket 70, a pinch valve piston 72, a spring 74, a retraction rod 76, a retraction knob 78, and a tension adjustment cap 80. IV tubing 18 runs inside tubing channel 62 such that the resilient bias provided by spring 74 tends to press the top of pinch valve piston 72 against IV tubing 18 to pinch closed the flow of sterile irrigating solution.

To use, pressure infuser bag 16 is pumped up to apply pressure to IV bag 14 and increase the maximum flow rate of the sterile irrigating solution. Pressure infuser bags are similar to blood pressure cuffs and are wrapped around IV bags to pressurize them. At rest, normally-closed pinch valve 12 pinches closed IV tubing 18 to block the flow of sterile irrigating solution to line adapter 10. When foot pedal 26 is pressed, it signals dental unit 20 to supply pressurized air to power dental handpiece 22. Air hose 28 is slaved off dental unit 20 so that, when foot pedal 26 is pressed, pressurized air is also supplied to pinch valve 12. As is shown by an inspection of FIG. 5, pressurized air supplied through inlet 66 pushes piston 72 against spring 74 and releases the pinch on IV tubing 18 to allow the flow of sterile irrigating solution to line adapter 10. Sterile irrigating solution flowing through line adapter 10 flows into handpiece 22 to irrigate the dental site then being worked on.

Pinch valve 12 includes tension adjustment cap 80 for adjusting the resilient bias imparted by spring 74. This adjustment is important because many dentists feather their foot control for more precise control of handpieces. By adjusting the tension, the flow of sterile irrigating solution can be made sufficient to irrigate a dental site when a foot control is being feathered and not fully depressed.

For re-use, the components of the sterile irrigation system are either disposable or easily sterilizable. Pressure infusers are generally disposable items, as are IV bags and the conventional IV tubing and connectors used to connect the IV bag to the handpiece line adapter. The handpiece line adapter is currently fabricated from anodized 2024 aluminum alloy with stainless steel port tubes and other components. It is easily sterilizable by autoclaving. Pinch valve 12, because it never comes into contact with a sterile surface, does not need to be sterilized.

The disclosed sterile water delivery system successfully demonstrates the advantages of a simple add-on apparatus for supplying sterile irrigating solution to a dental site which utilizes preexisting components of a high speed dental handpiece system to automatically control the flow of irrigating solution. Although the disclosed system is specialized, its teachings will find application in other areas where only expensive, complicated and hard-to-use stand-alone systems are presently available and, for those reasons, little used.

Those with skill in the art of the invention will readily see that the disclosed sterile water delivery system can also be used with some types of slow speed handpieces or with sonic scalers equipped with standard ISO connectors. The term dental handpiece, therefore, as used in this description and in the claims, includes any handheld instrument used for performing dental or surgical procedures in or around the mouth.

Those with skill in the art of the invention will also readily see that the described line adapter can be easily modified to work with other dental unit systems, such as 2-hole and 3-hole ISO connectors. Similarly, the foot control may be replaced by other control mechanisms for controlling dental handpieces. Also, an electrically operated dental unit can be modified so that the pinch valve is electrically actuated. Other modifications to the invention as described may be made, as might occur to one with skill in the field of the invention, within the intended scope of the claims. Therefore, all embodiments contemplated have not been shown in complete detail. Other embodiments may be developed without departing from the spirit of the invention or from the scope of the claims.

We claim:

1. An air controlled sterile irrigation system for providing sterile irrigating solution for dental procedures, comprising:
   (a) a sterilizable in-line adapter for connecting between an unmodified standard dental handpiece and a dental handpiece hose, the in-line adapter including an inlet port structurally adapted for receiving sterile irrigating solution from the dental handpiece hose and an outlet port structurally adapted for delivering sterile irrigating solution to the dental handpiece; and,
   (b) an air operated pinch valve for controlling the flow of sterile irrigating solution through an irrigating solution hose connected between a source of sterile irrigating solution and the inlet port for the sterilizable in-line adapter.

2. The air controlled sterile irrigation system according to claim 1, further comprising a dental unit for supplying pressurized air to the dental handpiece, wherein the dental unit supplies pressurized air to the pinch valve at the same time it supplies pressurized air to the dental handpiece.

3. The air controlled sterile irrigation system according to claim 1, the air operated pinch valve further comprising:
   (a) a resiliently biased pincher for pinching closed the irrigating solution hose;
   (b) an inlet for receiving pressurized air from a standard dental unit; and,
   (c) an air-controlled actuator connected to the pincher such that, when pressurized air is delivered through the inlet to the actuator, the actuator pushes the pincher against its resilient bias to incrementally open the irrigating solution hose.

4. The air controlled sterile irrigation system according to claim 3, further comprising a foot pedal control for connecting to a standard dental unit for controlling the delivery of pressurized air to the actuator.

5. An air controlled sterile irrigation system for providing sterile irrigating solution for dental procedures, comprising:
   (a) a sterilizable in-line adapter for connecting between an unmodified standard dental handpiece and a dental handpiece hose, the in-line adapter including an inlet port structurally adapted for receiving sterile irrigating solution from the dental handpiece hose and an outlet port structurally adapted for delivering sterile irrigating solution to the dental handpiece, wherein the sterilizable in-line adapter is adapted for connecting to a 4-hole ISO dental unit air-water hose and blocks the flow of water and chip air from the air-water hose through the in-line adapter;
   (b) an air operated pinch valve for controlling the flow of sterile irrigating solution through an irrigating solution hose connected between a source of sterile irrigating solution and the inlet port for the sterilizable in-line adapter.

6. A sterile irrigation system for providing sterile irrigating solution for dental procedures, comprising:
   (a) a sterilizable in-line adapter for connecting between an unmodified dental handpiece and a dental handpiece hose, the in-line adapter including an inlet port structurally adapted for receiving sterile irrigating solution from the dental handpiece hose and an outlet port structurally adapted for delivering sterile irrigating solution to the dental handpiece; and,
   (b) a pinch valve for controlling the flow of sterile irrigating solution through an irrigating solution hose connected between a source of sterile irrigating solution and the inlet port for the sterilizable in-line adapter.

7. The sterile irrigation system according to claim 6, further comprising a dental unit for supplying power to the dental handpiece, wherein the dental unit supplies power to the pinch valve at the same time it supplies power to the dental handpiece.

8. A method for providing sterile irrigating solution to a dental site for surgical and restorative procedures, comprising the steps of:

(a) providing a sterilizable in-line adapter connected between an unmodified dental handpiece and a dental handpiece hose, the in-line adapter including an inlet port connected to the dental handpiece hose and an outlet port connected to the dental handpiece;

(b) providing an air operated normally-closed pinch valve girdling an irrigating solution hose connected between a source of sterile irrigating solution and the inlet port for the sterilizable in-line adapter, wherein the pinch valve is connected through an air hose to a dental unit and wherein the dental unit is controlled by a controller for controlling the supply of pressurized air to the dental handpiece; and, (c) activating the controller to deliver pressurized air to the dental handpiece and simultaneously deliver pressurized air to the pinch valve to release the pinch valve and permit the flow of sterile irrigating solution through the irrigating solution hose into the inlet port for the in-line adapter and out the outlet port into the dental handpiece.

9. The method for providing sterile irrigating solution to a dental site for surgical and restorative procedures according to claim 8, further comprising the step of providing a foot control as the dental unit controller.

* * * * *